Sept. 17, 1968 R. S. MOORE Plant Pat. 2,834
ROSE PLANT
Filed March 27, 1967
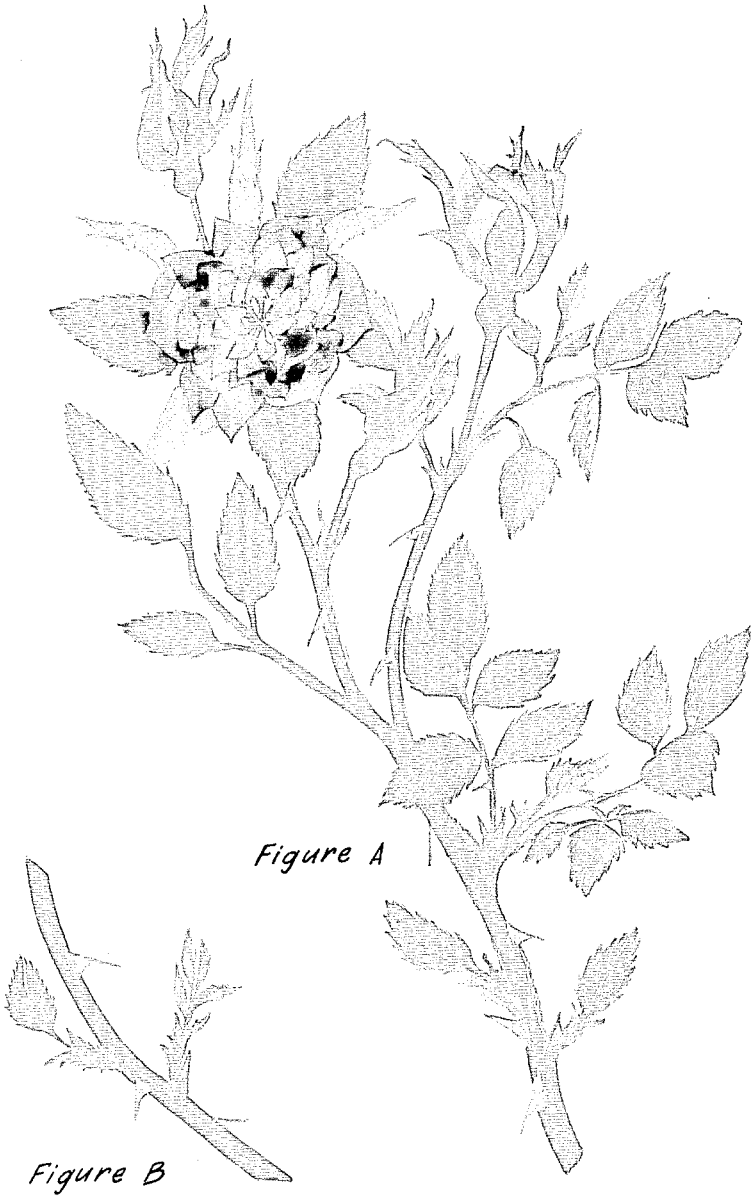
WITNESS
Janette Nunn Copley
INVENTOR
Ralph S. Moore United States Patent Office Plant Pat. 2,834
Patented Sept. 17, 1968

2,834
ROSE PLANT
Ralph S. Moore, 2519 E. Noble Ave.,
Visalia, Calif. 93277
Filed Mar. 27, 1967, Ser. No. 626,348
1 Claim. (Cl. Plt.—10)

The present invention relates to a new and distinct variety of hardy, dwarf, bush type rose of the miniature class; the variety being primarily characterized—as to novelty—by bright medium red buds and flowers which in general color effect are all over red color from the opening bud to the finished flower.

The variety is further characterized by:

An abundance of bloom, with flowers borne in loose clusters (rarely singly except on very young plants).

Moderate, slightly apple fragrance.

A plant which is vigorous, of rounded upright shape, and with dark green, glossy, small to medium small foliage with pointed leaflets; the flower being similar in size and form to the variety Dian (United States Plant Patent No. 1,808) but deeper shade of red and borne on somewhat stiffer stem. The plant, which has a normal average height of 12" to 14" at maturity, can easily be maintained at a lower height with occasional trimming.

A plant which grows and blooms satisfactorily both in the greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between an unnamed seedling (*Rosa wichuraiana* × Carolyn Dean), not patented, as the seed parent, and Little Buckaroo (United States Plant Patent No. 1,726) as the pollen parent.

Subsequent to origination of the variety I successfully asexually reproduced it, in my nursery located as aforesaid, by budding as well as by cuttings, the reproductions having run true in all respects.

The figure of the drawing allustrates a spray, including foliage, buds, flowers and thorns.

Referring now specifically to the new and distanct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers:

*Continuity.*—Intermittent to continuous throughout season.

*Frangrance.*—Moderate.

*Lasting quality.*—Better than average.

Flowers borne: Usually in loose clusters, several together, on medium length quite stiff (wire-like) stems.

Quantity of bloom: Average to above average both outside and in greenhouse.

Bud:

*Peduncle.*—Medium length; slender; wire-like; erect; light green; nearly smooth with occasional tiny reddish prickles.

*Before calyx breaks.*—Size—small. Form—pointed, with foliaceous appendages on surface of bud and foliaceous parts extending beyond the tip of the bud equal to one half or more of its length.

*Color.*—Medium green (in greenhouse) with sometimes a bronzy tint. As calyx breaks: color—red, shading to pale yellowish green at base; size—small.

*Form.*—Medium length; short-pointed.

*Opening.*—Opens well in all weather.

Bloom:

*Size when fully open.*—Small, 1" to 1¼".

*Petalage.*—Double—35 to 40 (sometimes more) petals arranged regularly. Sometimes a number of additional petaloids, tightly rolled inward around pistil.

*Form.*—Flat or slightly cupped at first; later at maturity remaining relatively flat or cupshaped with a few of outer petals rolled slightly outward.

Petals: Rather thick; stiff; satiny both inside and outside. Shape: outside petals—broad lanceolate (nearly round) with small acute tip; intermediate—lanceolate with acute tip; inside—narrow lanceolate with acute tip.

Color: Newly opened flower from plant grown indoors (March 1967) Visalia, Calif.

*Outside petal.*—Outside surface—Rose Red 724/3 (with darker shadings) blending into near white at base. Inside surface—Rose Red 724 (with darker shadings near petal tip) shading to near white at base.

*Intermediate petal.*—Outside surface—Rose Red 724/3 shading to white on lower ¼ of petal. Inside surface—Rose Red 724 (with blackish shadings on outer edge near petal tip) blending to near white on lower ¼ of petal.

*Inside petal.*—Outside surface—Rose Red 724/1 (with darker shading) blending to near white at petal base. Inside surface—Rose Red 724 or darker, near white at base.

General color effect: Newly opened flower—uniform medium red. Three days open—essentially same red color.

Behaviour: Spent blooms persist as flower ages, then petals drop clean.

Flower longevity (March—in greenhouse—1967), bush or pot—6 to 8 days or longer; outdoors—summer 1966—6 to 10 days. Cut flowers at living room temperature—4 to 6 days.

Reproductive organs:

*Stamens.*—Few to none; arranged regularly about pistil.

*Filiments.*—Short, often mixed with petaloids.

*Pollen.*—Little or none.

*Pistils.*—Average length and number.

*Styles.*—Medium length; bunched; near white.

*Stigma.*—Near white.

*Ovaries.*—All enclosed in calyx.

*Hips.*—None.

*Sepals.*—Permanent; spear shaped.

*Seeds.*—None.

Foliage:

*Leaves.*—Compound of five leaflets (occasionally 3); abundant; small; leathery; glossy.

*Leaflets.*—Shape—lanceolate, nearly oval; apex acute; base rounded; margin serrate. Color—medium to dark green; new growth often tinted bronze (outdoors). Rachis—medium strength; upper side grooved; under side sparsely thorny. Stipules—moderately long; narrow; short points, turning out an an angle of about 45 degrees.

Growth:

*Habit.*—Dwarf; bushy; rounded; much branched.

*Growth.*—Free; vigorous.

*Canes.*—Medium; slender.

*Main stems.*—Color—medium green. Thorns—moderately thorny; slender; medium length; hooked slightly downward with sharp points; color—light to medium brown. Prickles—none. Hairs—none.

*Branches.*—Color—medium green. Thorns—moderately thorny; medium length; hooked slightly downward; sharp points; medium length oval base. Prickles—none. Hairs—none.

*New shoots.*—Color—medium green (often tinted bronze outdoors). Thorns—moderately thorny; medium length; hooked slightly downward; sharp points; base oval; color—reddish-brown. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy dwarf, rounded, much branched, bush type, as illustrated and described, characterized by buds and flowers resembling the Dian miniature rose (U.S. Plant Patent No. 1,808) in general form but with deeper red color, the general color effect of the freshly opened flower being an all over red of uniform shade with little tendency to fade; and further characterized by a plant which is vigorous and yet compact in growth, easyt o propagate from cuttings; with small darker green foliage, more abundant and more mildew resistant than Dian rose, an abundance of bloom borne almost continuously throughout the growing season with flowers borne usually in loose clusters.

No references cited.

ROBERT E. BAGWILL, *Primary Examiner.*